United States Patent [19]

Ohura et al.

[11] 4,233,238

[45] Nov. 11, 1980

[54] PROCESS FOR PREPARING THIOUREA DIOXIDE

[75] Inventors: Osami Ohura; Osamu Fujimoto, both of Fuji, Japan

[73] Assignee: Tokai Denka Kogyo Kabushiki Kaisha, Tokyo, Japan

[21] Appl. No.: 55,788

[22] Filed: Jul. 9, 1979

[30] Foreign Application Priority Data

Jul. 25, 1978 [JP] Japan .................................. 53-89984

[51] Int. Cl.$^3$ ........................................... C07C 145/00
[52] U.S. Cl. .................................................. 260/513.7
[58] Field of Search ...................................... 260/513.7

[56] References Cited

U.S. PATENT DOCUMENTS

| 2,150,921 | 3/1939 | Havas | 260/513.7 |
| 2,347,446 | 4/1944 | Walker | 260/513.7 |
| 2,783,272 | 2/1957 | Young | 260/513.7 |

FOREIGN PATENT DOCUMENTS

| 45-17665 | 6/1970 | Japan | 260/513.7 |
| 50-62934 | 5/1975 | Japan | 260/513.7 |

*Primary Examiner*—Nicky Chan
*Attorney, Agent, or Firm*—Scully, Scott, Murphy & Presser

[57] ABSTRACT

According to this invention there is provided a process for preparing thiourea dioxide characterized in that in the production of thiourea dioxide by the reaction of thiourea and hydrogen peroxide in an aqueous solvent, the filtrate after separation of the crystals of thiourea dioxide after reaction is treated with an ion-exchange resin to remove side reaction products and impurities contained therein and then is used again as a reaction solvent.

7 Claims, No Drawings

PROCESS FOR PREPARING THIOUREA DIOXIDE

BACKGROUND OF THE INVENTION

1. Field of the Invention

This invention relates to a process for preparing thiourea dioxide (hereinafter referred to as "T.U.D.") in high yield and high purity.

2. Description of the Prior Art

Among the methods of production of T.U.D. there have been announced various reports on the method of its production by reaction of thiourea and hydrogen peroxide in a solvent.

The solvents used in such reported methods are broadly classified into non-aqueous and aqueous solvents.

The production of T.U.D. by the reaction of thiourea and hydrogen peroxide in a non-aqueous solvent (chlorinated solvents such as carbon tetrachloride and chloroform as well as lower aliphatic alcohols) has been proposed by German patent No. 917553, Italian patent No. 579119 and French patent No. 2040797. This proposed method is advantageous in that T.U.D. as the reaction product can all be recovered as crystals because it does not dissolve in the solvent. But such method is disadvantageous in that since the reaction of thiourea and hydrogen peroxide is a heterogeneous reaction, there are produced by-products in large quantities and these by-products do not dissolve in the solvent, so they are incorporated into the product T.U.D., thus causing the purity of the product to deteriorate, and besides the solvent used is lost in large quantities. Thus, an industrial adoption of such method involves many disadvantages.

On the other hand, in the case of production of T.U.D. in an aqueous solvent, the starting thiourea dissolves well in water and forms a homogeneous phase. Since the reaction of thiourea and hydrogen peroxide is very fast, their reaction in a homogeneous phase is advantageous in that the formation of by-products is less in quantity and T.U.D. can be obtained in high yield and high purity.

However, the said method is disadvantageous in that the quantity of T.U.D. crystals obtained becomes smaller because part of the reaction product T.U.D. is dissolved in the waste liquor after separation of the T.U.D. crystals produced. To eliminate this drawback, U.S. Pat. No. 2783272 and Japanese patent publication No. 17665/1970 propose a method in which such waste liquor is re-used as a reaction solvent to recover T.U.D. dissolved therein.

In the method proposed by U.S. Pat. No. 2783272, the waste liquor after reaction, as it is without any treatment, is re-used as a reaction solvent. According to such method, however, a repeated re-use of the waste liquor causes a correspondingly increasing accumulation in the reaction solution by-products, e.g. sulfuric acid, as well as impurities contained in the starting thiourea and hydrogen peroxide, resulting in that the yield and purity of T.U.D. lower. Japanese patent publication No. 17765/1970 purposes a method in which the waste liquor is treated with a carbonate or hydroxide of an alkaline earth metal, which is a metal of Group IIa of the Periodic Table, to neutralize the sulfuric acid contained therein, and after separation of the resulting precipitate of a sulfate the waste liquor is re-used as a reaction solvent. Treating the waste liquor in such a manner somewhat improves the yield and purity of T.U.D. as compared with the case where the said treatment is not applied, but does not afford a satisfactory result.

Although the above treating method can remove sulfuric acid contained in the waste liquor, it cannot remove other side reaction products and impurities derived from the starting thiourea and hydrogen peroxide, so that also in this treating method impurities accumulate in the reaction solution as the re-use of the treated waste liquor is repeated, which impurities not only hinder the reaction of thiourea and hydrogen peroxide but also contaminate the reaction product T.U.D., and thus a satisfactory result is not obtained. According to the Japanese patent publication referred to above which proposes this treating method, the neutralizer used therein does not promote the decomposition of T.U.D. However, in case such neutralizer is added in excess by mistake, there occurs a vigorous decomposition of T.U.D.; therefore, even if the waste liquor after neutralization is re-used to prepare T.U.D., there can be expected no improvement in the yield of T.U.D.

Furthermore, the neutralizer used in the waste liquor treatment is dissolved in the treated waste liquor, so the re-use of the latter causes lowering of the purity of the resulting T.U.D. This drawback is pointed out in Japanese patent public disclosure No. 62934/1975.

SUMMARY OF THE INVENTION

Having made a keen study about the method of removing by-products resulting from the reaction of thiourea and hydrogen peroxide and also removing impurities contained in the starting thiourea and hydrogen peroxide, we found that if the waste liquor after reaction is treated with an ion-exchange resin and then re-used as a reaction solvent, there can be obtained T.U.D. of a higher purity than has heretofore been achieved and that in high yield.

DESCRIPTION OF THE INVENTION

The method of treating the waste liquor after reaction with an ion-exchange resin is advantageous in that the impurities derived from the starting thiourea and hydrogen peroxide as well as the by-products resulting from the reaction of thiourea and hydrogen peroxide all can be removed; besides even with an excess ion-exchange resin used, the decomposition of T.U.D. is not promoted, and the waste liquor is not contaminated with such impurities during the treating process. Furthermore, in the method proposed by the Japanese patent publication No. 17665/1970 it is necessary to strictly control the pH of the waste liquor during its neutralization process and also to separate the resulting precipitate of a sulfate. On the other hand, the process of the present invention completely dispenses with such a troublesome operation, so its operation is very simple and easy.

Regarding the ion-exchange resins used in the present invention, even with an anion exchange resin alone there can be attained a little improvement over the method disclosed in the Japanese patent publication No. 17665/1970, but if it is used together with a cation exchange resin, the waste liquor treatment becomes more effective.

Anion exchange resins are used for the purpose of removing sulfate ion formed by the reaction of thiourea and hydrogen peroxide, phosphate ion incorporated from hydrogen peroxide, and chloride ion derived from thiourea. Anion exchange resins of any kind may be used in the present invention.

The use of cation exchange resin aims at removing heavy metal ion, alkali metal ion and alkaline earth metal ion derived from the starting thiourea and hydrogen peroxide, as well as by-products having a cation valency produced by the reaction of thiourea and hydrogen peroxide. But the by-products of unknown structure resulting from the reaction of thiourea and hydrogen peroxide are weakly basic substances, so the use of strongly acidic cation exchange resins is desirable to improve their removal.

Regarding the treating method, an ion-exchange resin may be added into the waste liquor, but passing the waste liquor through a column charged with an ion-exchange resin is more simple and convenient industrially.

To prevent the hydrolysis of T.U.D. contained in the waste liquor, it is preferable that the treatment temperature be maintained not higher than 15° C. and preferably not higher than 10° C.

The treating method of the present invention can be applied to all waste liquors obtained in the production of T.U.D. by the reaction of thiourea and hydrogen peroxide in an aqueous solvent no matter what the reaction condition and reaction system may be. However, if hydrogen peroxide remains in the waste liquor obtained, it can cause deterioration of an ion-exchange resin, so in such a case it is necessary to decompose the residual hydrogen peroxide in advance with a reducing agent such as sulfurous acid or sulfite, and then treat the waste liquor with an ion-exchange resin.

DESCRIPTION OF PREFERRED EMBODIMENTS

Reference examples and a working example of the present invention are given below, but these are for illustration only and are not intended to restrict the invention.

REFERENCE EXAMPLE (A)

25 g of thiourea was dissolved in 250 g of pure water and the solution cooled to 8–10° C., at which temperature was added 49 g of a 50% aqueous hydrogen peroxide solution over a period of 90 minutes while the reaction solution was stirred. Then, after ageing at 8–10° C. for 30 minutes with continued stirring of the reaction solution, the resulting T.U.D. was separated and 250 ml of the filtrate thereby obtained was re-used as the reaction solvent, and the reaction carried out in the same manner.

REFERENCE EXAMPLE (B)

T.U.D. was prepared by the method of Reference Example (A) and the filtrate thereby obtained was neutralized with calcium hydroxide to the pH value of 6.0 while the temperature was maintained at 8°–10° C. After separation of the resulting calcium sulfate, 250 ml of the filtrate thereby obtained was re-used as the reaction solvent, and the reaction repeated in the same manner.

EXAMPLE

T.U.D. was prepared by the method of Reference Example (A) and the filtrate thereby obtained was passed through a column charged with 25 ml of an anion exchange resin (Amberlite IRA-400) and 25 ml of a cation exchange resin (Amberlite IR-120B) while the filtrate temperature was maintained at 8–10° C. 250 ml of the resulting solution was used as the reaction solvent and the same procedure was repeated.

The yield, purity and property of the T.U.D.'s obtained in the above Reference Examples (A), (B) and working Example are shown together in table below.

|  |  | Crystal Yield | T.U.D Yield | Purity | Property |
| --- | --- | --- | --- | --- | --- |
| Reference Example (A) | Initial Reaction | 68.8% | 65.8% | 95.6% | White |
|  | 1st Re-Use of Filtrate | 66.4% | 55.9% | 84.2% | Yellow |
|  | 2nd Re-Use of Filtrate | 61.3% | 46.5% | 75.8% | " |
|  | 3rd Re-Use of Filtrate | 62.4% | 44.1% | 70.7% | " |
| Reference Example (B) | Initial Reaction | 69.1% | 66.1 | 95.6% | White |
|  | 1st Re-Use of Filtrate | 73.4% | 65.3% | 88.9% | " |
|  | 2nd Re-Use of Filtrate | 89.1% | 67.8% | 76.1% | Yellow |
|  | 3rd Re-Use of Filtrate | 78.6% | 54.5% | 69.4% | " |
| Example | Initial Reaction | 68.3% | 65.4% | 95.7% | White |
|  | 1st Re-Use of Filtrate | 83.0% | 79.9% | 96.3% | " |
|  | 2nd Re-Use of Filtrate | 84.9% | 81.3% | 95.8% | " |
|  | 3rd Re-Use of Filtrate | 84.5% | 81.5% | 96.4% | " |

We claim:

1. A process for preparing thiourea dioxide characterized in that in the production of thiourea dioxide by the reaction of thiourea and hydrogen peroxide in an aqueous solvent, the filtrate after separation of the crystals of thiourea dioxide after reaction is treated with both an anion exchange resin and a cation-exchange resin to remove side reaction products and impurities contained therein and then is used again as a reaction solvent in said process.

2. A process according to claim 1, in which said cation exchange resin is a strongly acidic cation exchange resin.

3. A process according to claim 1, in which the filtrate to be treated is passed through a column charged with the ion-exchange resins and is thereby treated.

4. A process according to claim 1, in which the treatment of the filtrate with an ion-exchange resin is carried out at a temperature not higher than 15° C.

5. A process according to claim 1, in which hydrogen peroxide remaining in the filtrate is decomposed in advance with a reducing agent and then the filtrate is subjected to the treatment with the ion-exchange resins.

6. The process of claim 4, in which said temperature is not higher than 10° C.

7. The process of claim 5, in which said reducing agent is selected from the group consisting of sulfurous acid and sulfite.

* * * * *